US00PP14996P2

(12) United States Plant Patent
Pieters

(10) Patent No.: US PP14,996 P2
(45) Date of Patent: Jul. 6, 2004

(54) CHRYSANTHEMUM PLANT NAMED 'GEDI TWO KIS'

(50) Latin Name: *Chrysanthemum morifolium*
Varietal Denomination: Gedi Two Kis

(75) Inventor: Dirk Pieters, Staden (BE)

(73) Assignee: Pieters Plant Production, BVBA, Staden (BE)

( * ) Notice: Subject to any disclaimer, the term of this patent is extended or adjusted under 35 U.S.C. 154(b) by 0 days.

(21) Appl. No.: 10/613,361

(22) Filed: Jul. 3, 2003

(51) Int. Cl.[7] ..... A01H 5/00
(52) U.S. Cl. ..... Plt./290

(58) Field of Search ..... Plt./290

(56) References Cited

U.S. PATENT DOCUMENTS

PP11,569 P 10/2000 Pieters
PP13,731 P3 4/2003 Pieters

*Primary Examiner*—Anne Marie Grunberg
*Assistant Examiner*—Annette H Para
(74) *Attorney, Agent, or Firm*—Knobbe, Martens, Olson & Bear, LLP

(57) ABSTRACT

A new and distinct Chrysanthemum plant cultivar is disclosed, characterized by a light bronze decorative inflorescence which naturally blooms in mid September. The plant has a rounded form and an extremely flexible habit.

1 Drawing Sheet

Figure 1:
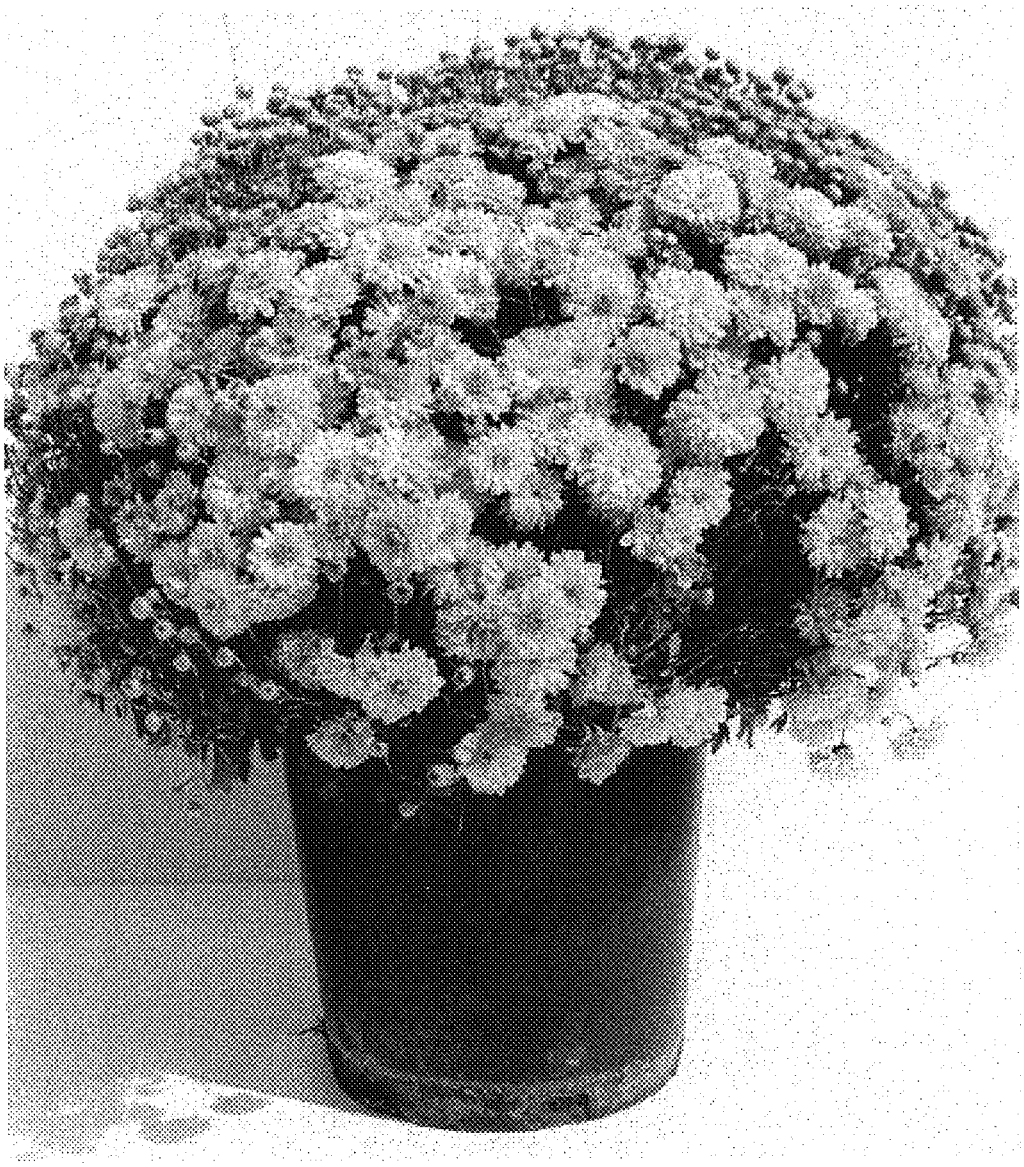

Latin name of the genus and species: *Chrysanthemum morifolium.*
Variety denomination: 'Gedi Two Kis'.

BACKGROUND OF THE INVENTION

The present invention relates to a new and distinct cultivar of decorative-type Chrysanthemum plant, herein after referred to by the cultivar name 'Gedi Two Kis.' The new cultivar is a product of hybridization of a female parent Chrysanthemum plant variety 'Red Elani' (undistributed in the United States, origin unknown) and a male parent Chrysanthemum plant variety 'Gedi Oro 8' (U.S. Plant Pat. No. 11,569). The new cultivar was discovered and selected by Dirk Pieters in Staden, Belgium, in October, 2000.

Asexual reproduction of the new cultivar by vegetative cuttings and tissue culture was performed in Staden, Belgium and in Oxnard, Calif., and has shown that the unique features of this cultivar are stable and reproduced true to type on successive generations.

SUMMARY OF THE INVENTION

The cultivar 'Gedi Two Kis' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Kis.' These characteristics in combination distinguish 'Gedi Two Kis' as a new and distinct Chrysanthemum cultivar:

1. Light bronze colored inflorescence.
2. Decorative-type inflorescence.
3. Naturally blooms in mid September.
4. Plant form is exceptionally round.
5. Plant has an extremely flexible habit.

Plants of the new cultivar are similar to plants of the female parent variety, 'Red Elani' in most horticultural characteristics. However, plants of the new cultivar have light bronze ray florets as compared to red ray florets of 'Red Elani.' Additionally, plants of the new cultivar have almost twice as many ray florets as 'Red Elani.' Further, the new variety is taller than 'Red Elani.'

Plants of the new cultivar are similar to plants of the male parent variety, 'Gedi Oro 8' in most horticultural characteristics, however the inflorescence of the new cultivar has more ray florets and less disc florets than plants of the male parent variety. The ray florets of the new variety are a lighter bronze in color, whereas the ray florets of the male parent variety, 'Gedi Oro 8' are darker bronze in color. Additionally, the new variety blooms approximately two weeks earlier than the male parent variety.

The new cultivar is similar to the commercial variety 'Gedi Two Sap' (U.S. Plant Pat. No. 13,731) in plant shape and flower type. In comparison to 'Gedi Two Sap', the new variety has a smaller diameter inflorescence with lighter bronze ray florets. The new variety is also taller and blooms approximately 3 weeks earlier than 'Gedi Two Sap.'

BRIEF DESCRIPTION OF THE PHOTOGRAPH

The photograph shows a plant of 'Gedi Two Kis.' One cutting was planted in a two-gallon container in May. The plant was grown outdoors in Oxnard, Calif.

DETAILED BOTANICAL DESCRIPTION

In the following description, color references are made to The Royal Horticultural Society Colour Chart except where general terms of ordinary dictionary significance are used. The following observations and measurements describe 110 day old plants grown in Oxnard, Calif., during the month of September. Light conditions were bright, and no artificial shading was used. The humidity was low and no rainfall occurred. The growing temperature ranged from 15° C. to 21° C. at night, with day temperatures ranging from 19° C. to 32° C. Measurements and numerical values represent averages of typical flowering types.

Botanical classification: *Chrysanthemum morifolium* cultivar 'Gedi Two Kis'.
Commercial classification: Garden-type Chrysanthemum.

PROPAGATION

Time to rooting: Approximately 7 to 14 days at approximately 21° C.
Root description: Fine, fibrous.

PLANT

Growth habit: Mounding herbaceous perennial.
Height: Approximately 33 cm.
Plant spread: Approximately 52 cm.
Growth rate: Moderate.
Branching characteristics: Free branching.
Length of lateral branches: Approximately 31 cm.
Number of leaves per lateral branch: Approximately 65.
Age of plant described: Approximately 110 days.

FOLIAGE

Leaf:
*Arrangement.*—Alternate.
*Average length.*—Approximately 3.4 cm.
*Average width.*—Approximately 1.9 cm.
*Shape of blade.*—Ovate.
*Apex.*—Cuspidate.
*Base.*—Attenuate.
*Attachment.*—Stalked.
*Margin.*—Palmately lobed.
*Texture of top surface.*—Lightly pubescent.
*Texture of bottom surface.*—Lightly pubescent.
*Color.*—Young foliage upper side: Near Green 137B. Young foliage under side: Near Green 138A. Mature foliage upper side: Near Green 137A. Mature foliage lower side: Near Yellow-green 147B. Venation upper side: Near Green 137D. Venation under side: Near Yellow-green 147C.
*Venation type.*—Net.
Petiole:
*Average length.*—Approximately 1.2 cm.
*Color.*—Near Green 137A.
*Diameter.*—Approximately 2 mm.
*Internode length.*—Approximately 2.3 cm.

BLOOM

Inflorescence:
*Flowering habit.*—Induced by darkness period greater than about 13.5 hours, approximately 46 days of appropriate day length required to induce and develop blooms.
*Inflorescence form.*—Decorative.
*Flower fragrance.*—Not present.
*Natural flowering season.*—Natural flowering begins between September 15 and September 25 in Southern California.
*Number of inflorescences per lateral branch.*—Approximately 54.
*Inflorescence diameter.*—Approximately 3 cm.
*Inflorescence depth.*—Approximately 1.1 cm.
*Inflorescence longevity on plant.*—Approximately 24 days.
*Persistence.*—Persistent.
Ray florets:
*Appearance.*—Matte.
*Texture.*—Smooth.
*Average number per flower.*—Approximately 162.
*Shape.*—Oblong.
*Aspect.*—Flat.
*Margin.*—Entire.
*Apex.*—Retuse.
*Length.*—Approximately 1.4 cm.
*Width.*—Approximately 5 mm.
*Color.*—Upper surface at first opening: Near Yellow-orange 22C. Upper surface at maturity: Near Yellow-orange 19B. Upper surface at fading: Near Yellow-orange 18B. Under surface at first opening: Near Yellow-orange 19C. Under surface at maturity: Near Yellow-orange 19C. Under surface at fading: Near Yellow-orange 18C.
Disc florets:
*Appearance.*—Matte.
*Textures.*—Smooth.
*Average number per flower.*—Approximately 9.
*Shape.*—Cylindric.
*Apex.*—Obtuse.
*Average length.*—Approximately 5 mm.
*Average width.*—Approximately 1 mm.
*Color.*—At first opening: Near Yellow 9C. At maturity: Near Yellow-orange 14B. At fading: Near Yellow 13B.
Peduncle:
*Length.*—At terminal end (shortest): Approximately 4.2 cm. At lateral end (longest): Approximately 12 cm.
*Angle to stem.*—Acute.
*Strength.*—Moderate.
*Color.*—Near Yellow-green 146A.
*Habit.*—Upright.
*Diameter.*—Approximately 2 mm.
*Texture.*—Lightly pubescent.
Inflorescence bud:
*Length.*—Approximately 7 mm.
*Diameter.*—Approximately 8 mm.
*Form.*—Globular.
*Color.*—Near Orange 26C.
Phyllaries (involucral bracts):
*Appearance.*—Matte.
*Texture.*—Lightly pubescent.
*Number.*—Approximately 83 throughout the inflorescence.
*Shape.*—Oblanceolate.
*Margin.*—Entire.
*Apex.*—Acute.
*Length.*—Approximately 8 mm.
*Width.*—Approximately 3 cm.
*Color.*—Upper side: Near Green 143A. Under side: Near Green 143A.

REPRODUCTIVE ORGANS

Ray florets:
*Number of pistils per floret.*—1.
*Stigma shape.*—2 branched.
*Stigma color.*—Near Yellow 9C.
*Style color.*—Near Yellow-green 154D.
*Style length.*—Approximately 5 mm.
*Stamens.*—Absent.
Disc florets:
*Number of pistils per florets.*—1.
*Stigma shape.*—2 branched.
*Stigma color.*—Near Yellow-orange 14B.

*Style length.*—Approximately 6 mm.
*Style color.*—Near Yellow-green 154D.
*Number of stamens per floret.*—Approximately 5.
*Anther shape.*—Tubular.
*Anther color.*—Near Yellow-orange 14A.
*Pollen color.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility has been observed.

Drought tolerance and cold tolerance: Neither resistance nor susceptibility has been observed.

What is claimed is:

1. A new and distinct cultivar of Chrysanthemum plant named 'Gedi Two Kis' as herein illustrated and described.

* * * * *